(12) United States Patent
Konno et al.

(10) Patent No.: US 7,132,409 B2
(45) Date of Patent: Nov. 7, 2006

(54) ADENOSINE DERIVATIVES AND USE THEREOF

(75) Inventors: Takashi Konno, Fukushima (JP); Kazuhiro Uemoto, Saitama (JP); Shinya Onuma, Saitama (JP); Yoshikazu Kato, Fukushima (JP)

(73) Assignees: Toa Eiyo Ltd., Tokyo (JP); Yamasa Corporation, Choshi (JP)

( * ) Notice: Subject to any disclaimer, the term of this patent is extended or adjusted under 35 U.S.C. 154(b) by 0 days.

(21) Appl. No.: 11/032,020

(22) Filed: Jan. 11, 2005

(65) Prior Publication Data

US 2005/0130930 A1     Jun. 16, 2005

Related U.S. Application Data

(63) Continuation of application No. 10/363,675, filed as application No. PCT/JP01/07791 on Sep. 7, 2001, now Pat. No. 6,936,596.

(30) Foreign Application Priority Data

Sep. 8, 2000 (JP) .............................. 2000-272979
Aug. 10, 2001 (WO) ....................... PCT/JP01/06922

(51) Int. Cl.
*A61K 31/70* (2006.01)
*C07H 19/167* (2006.01)

(52) U.S. Cl. .................. 514/46; 514/45; 514/256; 514/351; 514/359; 514/381; 536/27.22; 536/25.32; 536/22.1; 536/25.31; 536/28.5; 544/277; 546/296

(58) Field of Classification Search .................. 514/46, 514/256, 351, 359, 381, 45; 536/27.22, 25.32, 536/22.1, 25.31, 28.5; 544/277; 252/299.63; 546/296; 548/311.1
See application file for complete search history.

(56) References Cited

U.S. PATENT DOCUMENTS 5,039,797 A     8/1991 Clack et al.
5,229,505 A     7/1993 Bru-Magniez et al.
5,593,975 A *   1/1997 Cristalli ........................ 514/46
6,387,889 B1 *  5/2002 Endo et al. ................... 514/46

FOREIGN PATENT DOCUMENTS

| EP | 0 444 196 | 9/1991 |
| EP | 488336 | 6/1992 |
| JP | 57-140716 | 8/1982 |
| JP | 01-146895 | 6/1989 |
| JP | 5-9197 | 1/1993 |
| JP | 5-9198 | 1/1993 |
| JP | 2002-173427 | 6/2002 |
| JP | 2003-55395 | 2/2003 |
| WO | 00/12098 | 3/2000 |

OTHER PUBLICATIONS

Toichi Abiru, et al.: "The antihypertensive effect of 2-alkynyladenosines and their selective affinity for adenosine A2 receptors", European Journal of Pharmacology and Experimental Therapeutics, vol. 273, No. 1, pp. 320-326 (1995).

C.E. Crosson: "Adenosine receptor activation modulates intraocular pressure in rabbits" The Journal of Pharmacology and Experimental Therapeutics, vol. 273, No. 1, pp. 320-326 (1995).

* cited by examiner

Primary Examiner—Shaojia Anna Jiang
Assistant Examiner—Devesh Khare
(74) Attorney, Agent, or Firm—Oblon, Spivak, McClelland, Maier & Neustadt, P.C.

(57) ABSTRACT

2-(6-Cyano-1-hexyn-1-yl)adenosine, 2-(6-cyano-1-hexyn-1-yl)adenosine 5'-monophosphate, or salts thereof; and drugs containing the same as an active ingredient. The compounds have excellent effects of lowering ocular tension, promoting blood flow in retina, and protecting optic nerve failure and are highly soluble in water. Owing to these characteristics, the compounds are useful as drugs such as remedies for glaucoma and ocular hypertension.

21 Claims, No Drawings

ADENOSINE DERIVATIVES AND USE THEREOF

CROSS-REFERENCE TO RELATED APPLICATIONS

This application is a continuation application of U.S. application Ser. No. 10/363,675, pending, which is a 371 of PCT/JP01/07791 filed Sep. 7, 2001.

TECHNICAL FIELD

The present invention relates to adenosine derivatives which are useful as remedies for glaucoma and ocular hypertension, and to drugs containing the derivatives as active ingredients.

BACKGROUND ART

2-Alkynyladenosine derivatives, which have an alkynyl group at the 2-position of the adenosine base, have been accepted to be useful remedies for circulatory disorders such as hypertension (Japanese Patent No. 3053908). Also, the 2-alkynyladenosine derivatives have been known to exhibit an excellent effect of lowering ocular tension and to be a useful remedy for ophthalmological disorders, especially for glaucoma and ocular hypertension (WO00/12098).

However, the 2-alkynyladenosine derivatives, which have conventionally been reported to exhibit effect of lowering ocular tension, have the problem that they generally exhibit poor solubility in water. Poor solubility in water requires addition of a large amount of solubilizer when a liquid drug (e.g., an eye drop solution) is prepared, resulting in undesirable effects on stability and in terms of stimulation. In addition, interaction between the solubilizer and other additives may often occur, thereby raising limitations on preparation of drugs.

Accordingly, an object of the present invention is to provide an adenosine derivative which exhibits excellent pharmaceutical effects, such as effect of lowering ocular tension, and which have a high solubility in water, and drugs containing the derivative as an active ingredient.

DISCLOSURE OF THE INVENTION

In view of the foregoing, the present inventors synthesized a large number of adenosine derivatives having a cyano group at the end portion of the alkynyl group as represented by the following formula, and studied their effects in lowering ocular tension and their solubility in water:

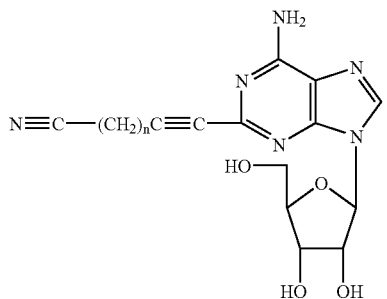

wherein n represents an integer of 2 or more.

Quite unexpectedly, the inventors found that 2-(6-cyano-1-hexyn-1-yl)adenosine (n=4) and phosphate thereof exhibit the same level of effect of lowering ocular tension as contrasted to the 2-alkynyladenosine derivatives reported in WO00/12098, effects of promoting blood flow in the retina and preventing optic nerve failure, and higher solubility in water, by a factor of several to some hundreds of times. Thus, the present inventors have determined that the mentioned compounds are useful remedies for glaucoma and ocular hypertension, especially when they are formulated as eye drop solutions, thereby achieving the invention.

Accordingly, the present invention provides 2-(6-cyano-1-hexyn-1-yl)adenosine, 2-(6-cyano-1-hexyn-1-yl)adenosine 5'-monophosphate, or salts thereof, and drugs containing any one of these compounds as an active ingredient.

BEST MODES FOR CARRYING OUT THE INVENTION

Examples of the 2-(6-cyano-1-hexyn-1-yl)adenosine salts or 2-(6-cyano-1-hexyn-1-yl)adenosine 5'-monophosphate salts of the present invention include acid addition salts such as inorganic acid salts (e.g., hydrochlorides, sulfates, and hydrobromides) and organic acid salts (e.g., oxalates, citrate, and malates); alkali metal salts such as sodium salts and potassium salts; alkaline earth metal salts such as calcium salts and magnesium salts; ammonium salts; and organic amine salts such as triethylammonium salts.

The 2-(6-cyano-1-hexyn-1-yl)adenosine of the present invention may be produced in accordance with the method described in Japanese Patent No. 3,053,908; through reaction of 2-halogenoadenosine with 6-cyano-1-hexyne in a solvent in the presence of a palladium catalyst and a copper compound.

Examples of the solvent include basic solvents such as triethylamine, tributylamine, N,N-diisopropylethylamine, trioctylamine, N,N,N',N'-tetramethyl-1,8-naphthalenediamine, N,N-dimethylaniline, N,N-diethylaniline, and pyridine; and aprotic polar solvents such as acetonitrile, N,N-dimethylformamide, dimethyl sulfoxide, N,N-dimethylacetamide, tetrahydrofuran, and 1,4-dioxane. These solvents may be employed singly or in combination.

Examples of the palladium catalyst include bis(acetonitrile)palladium dichloride, bis(triphenylphosphine)palladium dichloride, bis(benzonitrile)palladium dichloride, tetrakis(triphenylphosphine)palladium, and bis(triphenylphosphine)palladium diacetate. The palladium catalyst is preferably employed in an amount about 0.001 to 0.1 times by mol the amount of 2-halogenoadenosine.

Examples of the copper compound include copper halide such as cuprous iodide and cuprous bromide. The copper compound is preferably employed in an amount about 0.06 times by mol the amount of 2-halogenoadenosine.

The reaction is performed using 6-cyano-1-hexyne in an amount 1 to 3 times by mol the amount of 2-halogenoadenosine at 100 to 130° C. for 1 to 100 hours in the presence of a palladium catalyst and a copper compound. After completion of reaction, the product may be purified and isolated through a conventional method such as adsorption chromatography or recrystallization.

The 2-(6-cyano-1-hexyn-1-yl)adenosine 5'-monophosphate of the present invention may be produced through a reaction of 2-(6-cyano-1-hexyn-1-yl)adenosine with phosphorous oxyhalide in accordance with, for example, the Yoshikawa method [Tetrahedron Letters, 50, 5065–5068 (1967)].

Examples of the solvent include triesters of phosphoric acid, such as trimethyl phosphate and triethyl phosphate. A solvent mixture of any of these solvents and water may be employed. Examples of phosphorous oxyhalide include phosphorous oxychloride such as phosphoryl chloride (phosphorus oxychloride). The reaction is performed at −10 to 10° C. for 0.5 to 6 hours.

In separation of the target compound from the obtained reaction mixture, preferably, neutralization, salt formation reaction, or any other suitable reaction is performed, to thereby obtain the target compound transformed into a phosphate or a phosphate salt. Through a suitable combination of neutralization and salt formation reaction, the target compound of high purity can be obtained. The reaction mixture is reacted with an organic amine, to thereby form an organic amine salt of the target compound, and then the salt is separated. Subsequently, the salt is preferably neutralized in accordance with needs, and further transformed into other salts in accordance with needs.

When the target compound is separated as an organic amine salt, preferably chromatography is performed using a solution of the organic amine serving as an eluent.

The thus-obtained organic amine salt is allowed to react in water, in the presence of a mineral acid (e.g., hydrochloric acid, sulfuric acid, or phosphoric acid) at −10 to 10° C., to thereby yield the target compound of a phosphate salt form.

Other phosphate salt forms of the target compound may be produced through any of known salt formation reactions. Briefly, a phosphate alkali metal salt may be produced from a phosphate through reaction with an alkali metal hydroxide (e.g., lithium hydroxide, sodium hydroxide, or potassium hydroxide) in a solvent (e.g., an alcohol such as methanol or ethanol, N,N-dimethylformamide, water, or a mixture thereof) at 0° C. to room temperature. The thus-produced phosphate salt compounds are preferred because of their high solubility in water.

The thus-obtained compound may be isolated and purified in a manner similar to that described above.

The compounds of the present invention exhibit excellent effects of lowering ocular tension, promoting blood flow in the retina, and protecting optic nerve failure and are highly soluble in water. Therefore, the compounds are useful as pharmaceutical agents, such as remedies for glaucoma and ocular hypertension.

The drugs of the present invention are primarily administered non-orally, but may be administered orally. Examples of non-oral administration products include eye drop solutions, eye ointments, and injections, with eye drop solutions being preferred. Examples of oral administration products include solid products such as powders, granules, capsules, and tablets. These products may be produced through a general process, and pharmaceutically acceptable additives can be added to the compounds of the present invention.

In the preparation of eye drop solutions, if necessary, the following additives may be added to the compounds of the present invention: isotonicity agents such as sodium chloride and glycerin; stabilizers such as sodium edetate; preservatives such as benzalkonium chloride and parabens; or pH-adjusting agents such as sodium hydrogenphosphate, sodium dihydrogenphosphate, boric acid, sodium tetraborate (borax), hydrochloric acid, and sodium hydroxide. These eye drop solutions may be produced through a general process. The compounds of the present invention, having a high solubility in water, do not require any solubilizers for preparing drugs, and thus are particularly useful in producing such eye drop preparations that are very stable and induce no stimulation.

In the preparation of injections, any of the compounds of the present invention is dissolved in injection water, if necessary, together with pH-adjusting agents such as hydrochloric acid, sodium hydroxide, sodium hydrogenphosphate, or sodium dihydrogenphosphate; or isotonicity agents such as sodium chloride. The resultant solution is subjected to filtration under sterile conditions, and then placed in ampoules. In addition, the solution may be mixed with mannitol or gelatin and then freeze-dried under vacuum; in this case the resultant product is prepared into an injection upon use.

In the preparation of solid products for oral administration, the compounds of the present invention may be mixed with, if necessary, excipients such as lactose, starch, crystalline cellulose, calcium lactate, or calcium hydrogenphosphate; binders such as sucrose, hydroxypropyl cellulose, or polyvinylpyrrolidone; disintegrators such as carmellose calcium; or lubricants such as magnesium stearate or talc, to thereby produce a product through a general process. These solid products may be coated with enteric bases such as hydroxypropylmethyl cellulose phthalate and a methacrylic acid-methyl methacrylate copolymer, to thereby produce enteric drugs.

The dose of the 2-(6-cyano-1-hexyn-1-yl)adenosine, the 2-(6-cyano-1-hexyn-1-yl)adenosine 5'-monophosphate, or a salt thereof, which is an active ingredient of the drug of the present invention, is appropriately determined in accordance with the age, weight, and pathological conditions of the patient, and the product form of the drugs. Eye drop formulations containing the compounds of the present invention in an amount of 0.0001–10% (w/v) are preferably instilled or applied one to several times per day. In the case of oral agents or injections, the daily dose of the compounds of the present invention is usually 0.001–1,000 mg per person and per day, and the daily dose is preferably administered in a single dose, or in several divided doses.

EXAMPLES

The present invention will next be described in more detail by way of examples, which should not be construed as limiting the invention thereto.

Example 1

Production of 2-(6-cyano-1-hexyn-1-yl)adenosine

Under argon, to a solution of 2-iodoadenosine (420 mg, 1.07 mmol) and bis(triphenylphosphine)palladium dichloride (75 mg, 10 mol %) dissolved in N,N-dimethylformamide (10 mL), diisopropylamine (0.18 mL, 1.28 mmol, 1.2 eq.) and 6-cyano-1-hexyne (137 mg, 1.28 mmol, 1.2 eq.) were added, and, under ice-cooling conditions, cuprous iodide (10 mg, 5 mol %) was added thereto, followed by stirring at 50° C. for 24 hours. The reaction mixture was cooled to room temperature, and the solvent was removed under reduced pressure. The residue was purified by dry packed silica gel column chromatography (ethyl acetate:methanol=10:1), to thereby yield a compound of the present invention as a pale yellow powder (yield: 217 mg, percent yield: 55%).

mp: 91–94° C. ESI-MS m/z: 373(M+H)$^+$. $^1$H-NMR (DMSO-d$_6$+D$_2$O, 300 MHz)δ: 1.65–1.81 (m, 4H), 2.45–2.57 (m, 4H), 3.58(dd, 1H, J=3.1 Hz, 12.3 Hz), 3.70 (dd, 1H, J=2.9 Hz, 12.3 Hz), 4.00 (ddd, 1H, J=2.8 Hz, 2.9 Hz, 3.1 Hz), 4.16 (dd, 1H, J=2.8 Hz, 4.9 Hz), 4.54 (dd, 1H, J=4.9 Hz, 6.1 Hz), 5.88 (d, 1H, J=6.1 Hz), 8.35 (s, 1H). IR $\nu_{max}$(KBr): 3332, 2931, 2240, 1646, 1589, 1454, 1388, 1330, 1272, 1214, 1126, 1083 cm$^{-1}$.

Example 2

Production of triethylammonium 2-(6-cyano-1-hexyn-1-yl)adenosine 5'-monophosphate Under argon, A 2-(6-cyano-1-hexyn-1-yl)adenosine (2.41 g) was dissolved in triethyl phosphate (15 mL), and, under ice-cooling conditions, phosphorous oxychloride (25.2 mL, 3.9 eq.) was added thereto, followed by stirring at the same temperature for 5 hours. The reaction mixture was added dropwise to a 10% sodium hydroxide solution (300 mL), and the resultant mixture was washed with ether. The aqueous layer was separated and water was removed under reduced pressure, and the residue was purified by $C_{18}$ silica gel column chromatography (0.1M triethylammonium acetate buffer:acetonitrile=100:0 to 60:40). The thus-obtained fraction was concentrated, and the concentrate was subjected to $C_{18}$ silica gel column chromatography (water:acetonitrile=100:0 to 60:40), to thereby remove the triethylammonium acetate buffer. The residue was freeze-dried, to thereby yield 1.14 g of the above-titled compound as a colorless amorphous substance.

$^1$H-NMR(D$_2$O)δ: 1.10 (t, 9H, J=7.3 Hz), 1.57–1.74 (m, 4H), 2.34–2.42 (m, 4H), 3.02 (q, 6H, J=7.3 Hz), 3.91–4.03 (m, 2H), 4.20–4.22 (m, 1H), 4.32 (dd, 1H, J=4.4 Hz, 4.9 Hz), 4.52 (dd, 1H, J=4.9 Hz, 5.3 Hz), 5.89 (d, 1H, J=5.3 Hz), 8.28 (s, 1H). $^{31}$P-NMR(D$_2$O)δ: −2.25 (s). IR(KBr)$\nu_{max}$: 3337, 3179, 2938, 2678, 2243, 1654, 1637, 1594, 1457, 1380, 1068, 919 cm$^{-1}$.

Example 3

Production of 2-(6-cyano-1-hexyn-1-yl)adenosine 5'-monophosphate

A triethylammonium 2-(6-cyano-1-hexyn-1-yl)adenosine 5'-monophosphate (1.1 g) was dissolved in water (20 mL), and, under ice-cooling conditions, 1N HCl solution (2 mL) was added thereto, followed by standing for 10 minutes. After having been diluted with water (20 mL), the resultant mixture was filtered. The residue was washed with water (20 mL) and then with ethanol (20 mL×2), to thereby yield 617 mg of the above-titled compound as a colorless amorphous substance.

$^1$H-NMR(D$_2$O+NaOD)δ: 1.59–1.75 (m, 4H), 2.36–2.42 (m, 4H), 3.44–3.51 (m, 2H), 4.09–4.10 (m, 1H), 4.49 (dd, 1H, J=4.4 Hz, 4.9 Hz), 4.65 (dd, 1H, J=4.9 Hz, 5.5 Hz), 5.73 (d, 1H, J=5.5 Hz), 8.41 (s, 1H). $^{31}$P-NMR(D$_2$O+NaOD)δ: 1.44 (s). IR(KBr)$\nu_{max}$: 3330, 3125, 2934, 2241, 1690, 1592, 1398, 1227, 1081, 967 cm$^{-1}$.

Example 4

Production of monosodium 2-(6-cyano-1-hexyn-1-yl)adenosine 5'-monophosphate and disodium 2-(6-cyano-1-hexyn-1-yl)adenosine 5'-monophosphate A 2-(6-Cyano-1-hexyn-1-yl)adenosine 5'-monophosphate (800 mg) was dispersed in water (8 mL), and 1N sodium hydroxide solution (1.8 mL) was added thereto, followed by stirring for 0.5 hours. After having been diluted with water (10 mL), the resultant mixture was purified by $C_{18}$ silica gel column chromatography (water:acetonitrile=100:0 to 40:60), and the residue was freeze-dried, to thereby yield 130 mg of monosodium 2-(6-cyano-1-hexyn-1-yl)adenosine 5'-monophosphate and 709 mg of disodium 2-(6-cyano-1-hexyn-1-yl)adenosine 5'-monophosphate both as a colorless amorphous substance.

a: monosodium 2-(6-cyano-1-hexyn-1-yl)adenosine 5'-monophosphate

MS(ESI-)m/z: 451 (M$^+$)-H—Na. $^1$H-NMR(D$_2$O)δ: 1.60–1.76 (m, 4H), 2.37–2.46 (m, 4H), 3.95–4.09 (m, 2H), 4.23–4.26 (m, 1H), 4.35 (dd, 1H, J=4.2 Hz, 4.9 Hz), 4.55 (dd, 1H, J=4.9 Hz, 5.3 Hz), 5.92 (d, 1H, J=5.3 Hz), 8.31 (s, 1H). $^{31}$P-NMR(D$_2$O)δ: 0.56 (s). IR(KBr)$\nu_{max}$: 3338, 3190, 2942, 2244, 1647, 1594, 1383, 1070, 923 cm$^{-1}$. UV(H$_2$O)$\lambda_{max}$: 270, 232 nm.

b: disodium 2-(6-cyano-1-hexyn-1-yl)adenosine 5'-monophosphate

MS(ESI-)m/z: 451 (M$^+$)—H—2Na. $^1$H-NMR(D$_2$O)δ: 1.58–1.77 (m, 4H), 2.38–2.45 (m, 4H), 3.86–3.88 (m, 2H), 4.20–4.25 (m, 1H), 4.36 (dd, 1H, J=4.2 Hz, 4.9 Hz), 4.62 (dd, 1H, J=4.9 Hz, 5.5 Hz), 5.94 (d, 1H, J=5.5 Hz), 8.48 (s, 1H). $^{31}$P-NMR(D$_2$O)δ: 1.33 (s). IR(KBr)$\nu_{max}$: 3368, 2244, 1654, 1593, 1368, 1089, 978 cm$^{-1}$. UV(H$_2$O)$\lambda_{max}$: 270, 232 nm.

Referential Example 1

Production of 2-(7-cyano-1-heptyne-1-yl)adenosine

Under argon, to a solution of 2-iodoadenosine (200 mg, 0.51 mmol) and bis(triphenylphosphine)palladium dichloride (36 mg, 10 mol %) dissolved in N,N-dimethylformamide (5 mL), triethylamine (0.09 mL, 0.61 mmol, 1.2 eq.) and 7-cyano-1-heptyne (74 mg, 0.1 mmol, 1.2 eq.) were added, and, under ice-cooling conditions, cuprous iodide (10 mg, 5 mol %) was added thereto, followed by stirring at 60° C. for 24 hours. The reaction mixture was cooled to room temperature, and the solvent was removed under reduced pressure. The residue was purified by dry packed silica gel column chromatography (chloroform:methanol=10:1), to thereby yield the above-titled compound as a pale yellow powder (yield: 77 mg, percent yield: 39%).

mp: 99–101° C. ESI-MS m/z: 387(M+H)$^+$. H-NMR (DMSO-d$_6$+D$_2$O, 300 MHz)δ: 1.51–1.67 (m, 6H), 2.40–2.52 (m, 4H), 3.56 (dd, 1H, J=3.5 Hz, 12.3 Hz), 3.68 (dd, 1H, J=3.3 Hz, 12.3 Hz), 3.97 (ddd, 1H, J=3.1 Hz, 3.3 Hz, 3.5 Hz), 4.13 (dd, 1H, J=3.1 Hz, 5.0 Hz), 4.53 (dd, 1H, J=5.0 Hz, 6.0 Hz), 5.86 (d, 1H, J=6.0 Hz), 8.37 (s, 1H). IR$\nu_{max}$ (KBr): 3332, 2931, 2865, 2240, 1646, 1589, 1454, 1388, 1330, 1272, 1218, 1122, 1083 cm$^{-1}$.

The following compounds were employed in the Test Examples hereinbelow.

(In Test Example 1)
Compound 1 (invention): 2-(6-cyano-1-hexyn-1-yl)adenosine (synthesized in Example 1)
Compound 2 (invention): disodium 2-(6-cyano-1-hexyn-1-yl)adenosine 5'-monophosphate (synthesized in Example 4)
Referential Compound 1: 2-(5-cyano-1-pentyn-1-yl)adenosine (described in Japanese Patent No. 3053908)
Referential Compound 2: 2-(7-cyano-1-heptyn-1-yl)adenosine (synthesized in Referential Example 1)
Referential Compound 3: 2-cyclopentylethynyladenosine Referential Compound 4: 2-(1-octyn-1-yl)adenosine
Referential Compound 5: 2-(6-phthalimidyl-1-hexyn-1-yl)adenosine
Referential Compound 6: 2-(1-hexyn-1-yl)adenosine-4'-methylcarboxamide (these four compounds are described in WO00/12098)

(In Test Example 2)
Compound 1 (invention): 2-(6-cyano-1-hexyn-1-yl)adenosine (synthesized in Example 1)
Compound 2 (invention): disodium 2-(6-cyano-1-hexyn-1-yl)adenosine 5'-monophosphate (synthesized in Example 4)
Referential Compound 3: 2-cyclopentylethynyladenosine
Referential Compound 4: 2-(1-octyn-1-yl)adenosine
Referential Compound 5: 2-(6-phthalimidyl-1-hexyn-1-yl)adenosine
Referential Compound 6: 2-(1-hexyn-1-yl)adenosine-4'-methylcarboxamide (these four compounds are described in WO00/12098)

Test Example 1

Each of the mentioned compounds was dissolved in saline containing polysorbate 80 (hereinafter the saline will be referred to as "eye drop base A") or in a borate buffer (pH 7.0) containing polysorbate 80 (hereinafter the solution will be referred to as "eye drop base B") (polysorbate 80 content of each base: 5 mg/mL).

Japanese white rabbits (male; Kitayama Labes Co., Ltd.) (weight: 2.7–3.9 kg) were employed in the test for measuring ocular tension. The rabbits were retained in a box-type fixation apparatus during the test.

The ocular tension of each rabbit was measured by use of a Model 30 Classic Pneumatonometer (product of Mentor) without anesthesia. Before the ocular tension was measured, 0.4% oxybuprocaine hydrochloride (Benoxil 0.4% eye drop solution, product of Santen Pharmaceutical Co., Ltd.) was instilled into the eyes of each rabbit, to thereby anesthetize the surface of the cornea. The ocular tension of each rabbit was measured several times at predetermined intervals. Three measurements of ocular tension, as measured when a constant value was reached, were averaged, and the average value was employed as representing the ocular tension.

A 0.1% solution of each test compound (50 µL) was instilled to one eye of each of the respective rabbits, and simultaneously the eye drop base (50 µL) was instilled to the other eye. The ocular tensions of both eyes were measured 60 minutes before instillation of the test compound; 0 minute immediately before instillation; and 30, 60, 90, 120, 150, 180, 240, 300, 360, 420, and 480 minutes after instillation. Four to six rabbits were employed for each test compound. For control, each eye drop base was instilled to both eyes of rabbits, and the ocular tension thereof was measured in a manner similar to that described above.

For each test compound, the effect of lowering ocular tension was evaluated on the basis of the following values: the area under the curve of time versus change in difference between the ocular tension of the eye to which the test compound was instilled and that of the eye to which the eye drop base was instilled (hereinafter the area will be abbreviated as AUC (mmHg·min)); and the maximum value of difference between the ocular tension of the eye to which the test compound was instilled and that of the eye to which the eye drop base was instilled (hereinafter the value will be abbreviated as $E_{max}$ (mmHg)).

The AUC and $E_{max}$ of each test compound are shown in Table 1.

TABLE 1

| Test compound | AUC (mmHg · min) | $E_{max}$ (mmHg) | Eye drop base |
|---|---|---|---|
| Compound 1 (invention) | −1303.1 | −4.3 | B |
| Compound 2 (invention) | −1965.0 | −6.0 | B |
| Referential Compound 1 | −584.0 | −3.0 | B |
| Referential Compound 2 | −844.5 | −2.6 | B |
| Referential Compound 3 | −1532.7 | −4.4 | B |
| Referential Compound 4 | −1093.5 | −4.2 | A |
| Referential Compound 5 | −1471.0 | −6.3 | A |
| Referential Compound 6 | −1838.3 | −6.0 | A |
| Eye drop base A | −30.4 | −0.4 | — |
| Eye drop base B | −31.5 | −0.2 | — |

Test Example 2

Each of the test compounds was dispersed in an isotonic borate buffer (pH 7.0). The resultant mixture was shaken at 20° C. for 6 hours and then centrifuged. The concentration of the test compound in the supernatant was measured through HPLC for calculation of saturation solubility of the compound. The results are shown in Table 2.

(Measurement Conditions)
Detector: UV absorptiometer (wavelength: 270 nm)
Column: ODS column (inner diameter 4.6 mm, length 15 cm)
Mobile phase: An acetonitrile/triethylammonium acetate buffer (pH 7) mixture
Flow rate: 0.8 mL/min

TABLE 2

| Test compound | Saturation solubility (mg/mL) |
|---|---|
| Compound 1 (invention) | 16.6 |
| Compound 2 (invention) | >200 |
| Referential Compound 3 | 1.4 |
| Referential Compound 4 | 0.3 |
| Referential Compound 5 | 0.7 |
| Referential Compound 6 | 0.5 |

As is apparent from Table 1, the compounds of the present invention exhibit higher effects of lowering ocular tension as compared with compounds having an analogous structure (Referential Compounds 1 and 2), and comparable activity to compounds described in WO00/12098. Furthermore, as shown in Table 2, the compounds of the present invention exhibit excellent solubility in water as compared with compounds described in WO00/12098. Thus, the compounds of the present invention satisfy the mentioned requirements; i.e., effect of lowering ocular tension and solubility to water.

Moreover, from the study of the compounds of the present invention performed on rabbits, with respect to effects on blood diameter in retina and effects on blood flow, Compound 1 of the present invention was found to exhibit particularly excellent effects of promoting vasodilatation and blood flow in the retina. From the study of the compounds of the present invention performed on a model of retina failure induced through reperfusion after transient ischemia in rat, with respect to effects on optic nerve failure, Compound 1 of the present invention was found to exhibit particularly excellent effects of protecting optic nerve failure.

Example 5

Eye Drop Solution

| | |
|---|---|
| 2-(6-Cyano-1-hexyn-1-yl)adenosine | 0.1 g |
| Boric acid | 1.19 g |
| Borax (decahydrate) | 0.08 g |
| Sodium chloride | 0.27 g |
| Benzalkonium chloride | 0.01 g |
| Sterilized water | appropriate amount |
| Total | 100 mL |

An eye drop solution was prepared in accordance with the above formula. The resultant eye drop solution was subjected to sterile filtration, and then placed in polypropylene-made eye drop containers (5 mL for each container).

Example 6

Eye Drop Solution

| | |
|---|---|
| 2-(6-Cyano-1-hexyn-1-yl)adenosine | 0.1 g |
| Boric acid | 1.19 g |
| Borax (decahydrate) | 0.08 g |
| Sodium chloride | 0.27 g |
| Methyl p-hydroxybanzoate | 0.1 g |
| Propyl p-hydroxybanzoate | 0.05 g |
| Sterilized water | appropriate amount |
| Total | 100 mL |

An eye drop solution was prepared in accordance with the above formula. The resultant eye drop solution was subjected to sterile filtration, and then placed in polypropylene-made eye drop containers (5 mL for each container).

Example 7

Eye Drop Solution

| | |
|---|---|
| 2-(6-Cyano-1-hexyn-1-yl)adenosine | 0.1 g |
| Boric acid | 1.19 g |
| Borax (decahydrate) | 0.08 g |
| Sodium chloride | 0.27 g |
| Chlorobutanol | 0.5 g |
| Sterilized water | appropriate amount |
| Total | 100 mL |

An eye drop solution was prepared in accordance with the above formula. The resultant eye drop solution was subjected to sterile filtration, and then placed in polypropylene-made eye drop containers (5 mL for each container).

Example 8

Injection

| | |
|---|---|
| 2-(6-Cyano-1-hexyn-1-yl)adenosine | 0.5 g |
| Sodium chloride | 9 g |
| Injection water | appropriate amount |
| Total | 100 mL |

An injection was prepared in accordance with the above formula. The resultant injection was subjected to sterile filtration, and then placed in glass ampoules (2 mL per ampoule).

Example 9

Oral Administration Agent

| | |
|---|---|
| 2-(6-Cyano-1-hexyn-1-yl)adenosine | 5 mg |
| Lactose | 93 mg |
| Potato starch | 30 mg |
| Crystalline Cellulose | 15 mg |
| Hydroxypropyl Cellulose | 5 mg |
| Magnesium stearate | 2 mg |
| Total | 150 mg (per tablet) |

In accordance with the above formula, the compound of the present invention, lactose, potato starch, crystalline cellulose, and hydroxypropyl cellulose were mixed, and water was added to the resultant mixture. Subsequently, the mixture was kneaded, and then granulated through pressing with a screen. After the resultant granules were dried, magnesium stearate was added to the dried granules, to thereby produce tablets.

Test Example 3

Stability of Eye Drop Solutions

Eye drop solutions produced in Examples 5 to 7 were left to stand at 40° C. After one month, the content (percent residue, %) of the compound of the present invention in each of the solutions was measured by means of high performance liquid chromatography (HPLC) under the same conditions as Test Example 2. The results are shown in Table 3.

TABLE 3

| | Percent residue (%) |
|---|---|
| Example 5 | 101.4 |
| Example 6 | 100.5 |
| Example 7 | 101.8 |

As is apparent from Table 3, the eye drop solutions of the present invention were found to exhibit excellent stability.

INDUSTRIAL APPLICABILITY

The compounds of the present invention exhibit excellent effects of lowering ocular tension, promoting blood flow in retina, and protecting optic nerve failure, and have a high solubility in water. Owing to these characteristics, the above compounds are useful as drugs such as remedies for glaucoma and ocular hypertension. When the compounds of the present invention are used in forms of water-soluble liquid agents, neither addition of solubilizer or other agents nor heat treatment is required, thereby improving the quality and stability of the liquid agents. Particularly, the compounds of the present invention are suitable for use as water-soluble drugs, such as eye drop solutions or injections.

The invention claimed is:
1. 2-(6-cyano-1-hexyn-1-yl)adenosine, 2-(6-cyano-1-hexyn-1-yl)adenosine 5'-monophosphate, or a salt of any of these compounds.
2. The compound of claim 1, which is 2-(6-cyano-1-hexyn-1-yl)adenosine.
3. The compound of claim 1, which is 2-(6-cyano-1-hexyn-1-yl)adenosine 5'-monophosphate.
4. The compound of claim 1, which is a salt of 2-(6-cyano-1-hexyn-1-yl)adenosine.
5. The compound of claim 1, which is a salt of 2-(6-cyano-1-hexyn-1-yl)adenosine 5'-monophosphate.
6. The compound of claim 5, which is a monosodium salt of 2-(6-cyano-1-hexyn-1-yl)adenosine 5'-monophosphate.
7. The compound of claim 5, which is a disodium salt of 2-(6-cyano-1-hexyn-1-yl)adenosine 5'-monophosphate.
8. A drug comprising, as an active ingredient, 2-(6-cyano-1-hexyn-1-yl)adenosine, 2-(6-cyano-1-hexyn-1-yl)adenosine 5'-monophosphate, or a salt of any of these compounds.
9. The drug of claim 8, which comprises as the active ingredient 2-(6-cyano-1-hexyn-1-yl)adenosine.
10. The drug of claim 8, which comprises as the active ingredient 2-(6-cyano-1-hexyn-1-yl)adenosine 5'-monophosphate.
11. The drug of claim 8, which comprises as the active ingredient a salt of 2-(6-cyano-1-hexyn-1-yl)adenosine.
12. The drug of claim 8, which comprises as the active ingredient a salt of 2-(6-cyano-1-hexyn-1-yl)adenosine 5'-monophosphate.
13. The drug of claim 12, which comprises as the active ingredient a monosodium salt of 2-(6-cyano-1-hexyn-1-yl)adenosine 5'-monophosphate.
14. The drug of claim 12, which comprises as the active ingredient a disodium salt of 2-(6-cyano-1-hexyn-1-yl)adenosine 5'-monophosphate.
15. A pharmaceutical composition comprising 2-(6-cyano-1-hexyn-1-yl)adenosine, 2-(6-cyano-1-hexyn-1-yl)adenosine 5'-monophosphate, or a salt of any of these compounds, and a pharmacologically acceptable carrier therefor.
16. The pharmaceutical composition of claim 15, which comprises 2-(6-cyano-1-hexyn-1-yl)adenosine.
17. The pharmaceutical composition of claim 15, which comprises 2-(6-cyano-1-hexyn-1-yl)adenosine 5'-monophosphate.
18. The pharmaceutical composition of claim 15, which comprises a salt of 2-(6-cyano-1-hexyn-1-yl)adenosine.
19. The pharmaceutical composition of claim 15, which comprises a salt of 2-(6-cyano-1-hexyn-1-yl)adenosine 5'-monophosphate.
20. The pharmaceutical composition of claim 19, which comprises a monosodium salt of 2-(6-cyano-1-hexyn-1-yl)adenosine 5'-monophosphate.
21. The pharmaceutical composition of claim 19, which comprises a disodium salt of 2-(6-cyano-1-hexyn-1-yl)adenosine 5'-monophosphate.

* * * * *